United States Patent
Gillman et al.

(10) Patent No.: US 11,065,057 B2
(45) Date of Patent: Jul. 20, 2021

(54) DEVICES, SYSTEMS, AND METHODS FOR REDUCING AND FIXING FRACTURED BONES

(71) Applicant: Bullseye Hip Replacement, LLC, Las Vegas, NV (US)

(72) Inventors: Michael Gillman, Laguna Beach, CA (US); Benjamin A. Gillman, Laguna Beach, CA (US)

(73) Assignee: Bullseye Hip Replacement, LLC, Las Vegas, NV (US)

( * ) Notice: Subject to any disclaimer, the term of this patent is extended or adjusted under 35 U.S.C. 154(b) by 243 days.

(21) Appl. No.: 15/921,437

(22) Filed: Mar. 14, 2018

(65) Prior Publication Data

US 2018/0263700 A1    Sep. 20, 2018

Related U.S. Application Data

(60) Provisional application No. 62/471,825, filed on Mar. 15, 2017.

(51) Int. Cl.

| | | |
|---|---|---|
| *A61B 17/17* | (2006.01) | |
| *A61B 17/80* | (2006.01) | |
| *A61B 34/10* | (2016.01) | |
| *G16H 30/40* | (2018.01) | |

(Continued)

(52) U.S. Cl.
CPC .............. *A61B 34/10* (2016.02); *A61B 17/17* (2013.01); *A61B 17/1703* (2013.01); *A61B 17/1717* (2013.01); *A61B 17/1728* (2013.01); *A61B 17/1778* (2016.11); *A61B 17/8061* (2013.01); *A61B 17/8866* (2013.01); *G16H 30/40* (2018.01); *A61B 17/1764* (2013.01); *A61B 2017/568* (2013.01); *A61B 2034/102* (2016.02);

(Continued)

(58) Field of Classification Search
CPC . A61B 17/17; A61B 17/1703; A61B 17/1728; A61B 17/80; A61B 17/8028; A61B 17/8052; A61B 17/8057; A61B 17/8061; A61B 17/8866; A61B 2017/568
See application file for complete search history.

(56) References Cited

U.S. PATENT DOCUMENTS

| | | | |
|---|---|---|---|
| 7,896,886 B2 | 3/2011 | Orbay et al. | |
| 9,775,657 B2* | 10/2017 | Bernstein | ........... A61B 17/8057 |
| 10,080,599 B2* | 9/2018 | Caldarella | .......... A61B 17/8085 |

(Continued)

FOREIGN PATENT DOCUMENTS

| | | |
|---|---|---|
| EP | 2822485 B1 | 8/2017 |
| WO | WO-2018170162 A1 | 9/2018 |

*Primary Examiner* — Eric S Gibson
(74) *Attorney, Agent, or Firm* — Fisherbroyles; Charles Hagadorn

(57) ABSTRACT

A method of reducing a fractured bone of a patient is disclosed. The method may include generating a fractured bone surface image from image data of the fractured bone structure of the patient. A reduced bone surface image of the fractured bone structure of the patient may be formed. In some embodiments, an implant image may be superimposed in an installation position on the reduced bone surface image. A patient specific jig image may be superimposed proximate the implant image and the bone image, according to the installation position of the implant. In some embodiments, control data from the patient specific jig image may be generated.

5 Claims, 12 Drawing Sheets

(51) Int. Cl.
  *A61B 17/88* (2006.01)
  *A61B 17/56* (2006.01)
(52) U.S. Cl.
  CPC ... *A61B 2034/105* (2016.02); *A61B 2034/108* (2016.02)

(56) References Cited

U.S. PATENT DOCUMENTS

| | | | |
|---|---|---|---|
| 2007/0276405 A1* | 11/2007 | Huebner | A61B 17/80 606/105 |
| 2009/0198277 A1* | 8/2009 | Gordon | A61B 17/8076 606/248 |
| 2009/0312758 A1* | 12/2009 | Petit | A61B 17/82 606/60 |
| 2011/0106182 A1* | 5/2011 | Reisberg | A61B 17/82 606/324 |
| 2011/0301655 A1* | 12/2011 | Price | A61B 17/8061 606/86 R |
| 2012/0271366 A1 | 10/2012 | Katrana et al. | |
| 2013/0090695 A1* | 4/2013 | Bernstein | A61B 17/80 606/281 |
| 2014/0195205 A1 | 7/2014 | Benker et al. | |
| 2015/0051650 A1* | 2/2015 | Verstreken | G06F 19/00 606/281 |
| 2015/0190143 A1* | 7/2015 | Tarabichi | A61B 17/157 623/20.36 |
| 2016/0113661 A1* | 4/2016 | Gillman | A61B 17/1767 606/88 |
| 2016/0192970 A1* | 7/2016 | Dayton | A61B 17/80 606/281 |
| 2016/0367300 A1* | 12/2016 | Caldarella | A61B 17/064 |
| 2018/0256221 A1* | 9/2018 | Koay | A61B 17/8061 |
| 2018/0263700 A1* | 9/2018 | Gillman | A61B 17/1703 |
| 2018/0317986 A1* | 11/2018 | Jackman | A61B 17/151 |
| 2018/0360509 A1* | 12/2018 | Caldarella | A61B 17/808 |
| 2019/0142485 A1* | 5/2019 | Garcia | A61B 17/8076 606/291 |

\* cited by examiner

DEVICES, SYSTEMS, AND METHODS FOR REDUCING AND FIXING FRACTURED BONES

CROSS-REFERENCE

This application claims the benefit of U.S. Provisional Application No. 62/471,825, filed Mar. 15, 2017, the entire disclosure of which is incorporated herein by reference.

BACKGROUND OF THE INVENTION

Technical Field

The present disclosure relates to systems, devices, and methods for bone fracture repair, and more particularly, to patient-specific bone fracture repair devices, including methods of manufacturing and using such devices for achieving accurate fracture reduction and placement of implants based on computer generated imaging of a patient.

Description of the Related Art

One method of repairing fractured bones is to reduce the bone fracture and then fix the fractured bone in a reduced position. Improper reduction and fixing may lead to pain and reduced movement or use of extremities or other parts of the body. An orthopedic surgeon performing a fracture repair procedure seeks to ensure, through surgery, accurate reduction and fixation of the bone through proper reduction of the bone and placement of implants to fix the reduced bone. Improper reduction of a fractured bone can result in damage to the joints and pain in other areas of the body as a result of the body's attempt compensate for the improper reduction and fixation.

With the assistance of computer generated data derived from CT, MRI, or other scans, such as X-rays, surgeons can more effectively determine proper positions of properly reduced bones in a patient through 3-D modeling and rendering; however, accuracy and simplicity of existing devices and methods remain limited due to a variety of factors.

SUMMARY OF THE INVENTION

A method of reducing a fractured bone of a patient is disclosed. The method may include generating a fractured bone surface image from image data of the fractured bone structure of the patient. A reduced bone surface image of the fractured bone structure of the patient may be formed. In some embodiments, an implant image may be superimposed in an installation position on the reduced bone surface image. A patient specific jig image may be superimposed proximate the implant image and the bone image, according to the installation position of the implant. In some embodiments, control data from the patient specific jig image may be generated.

In some embodiments, a physical patient specific jig based on the control data may be generated. The implant image may comprise a bone facing surface image having a shape that corresponds to a shape of the reduced bone surface image at the installation position. The patient specific jig image may comprise a bone facing surface image having a shape that corresponds to a shape of the reduced bone surface image at the installation position. The patient specific jig image may comprise an implant facing surface image shaped to receive a reduction tool in a predetermined orientation.

In some embodiments the implant image may comprise an aperture image therethough, the aperture image shaped to receive a fastener for coupling the implant to the reduced bone surface image. The patient specific jig image may comprise an implant coupling image shaped to releasably couple the patient specific jig image to the implant image.

The implant image may comprise an implant body having an outer perimeter. The patient specific jig image may comprise an outer perimeter. A first portion of the outer perimeter of the patient specific jig image may be shaped to match a first portion of the outer perimeter of the implant body.

In some embodiments, forming a reduced bone surface image of the fractured bone structure of the patient may comprise forming a surface image of a corresponding contralateral bone of the patient. In some embodiments, forming a reduced bone surface image of the fractured bone structure of the patient may comprise reducing the fractured bone surface image to form the reduced bone surface.

A method of reducing a fractured bone of a patient is disclosed. The method may comprise generating a fractured bone surface image from image data of the fractured bone structure of the patient. A reduced bone surface image of the fractured bone structure of the patient may be formed. A bone reduction tool image may be superimposed in an installation position on the reduced bone surface image. A patient specific jig image may be superimposed proximate the bone reduction tool image and the bone image according to the installation position of the bone reduction tool. Control data from the patient specific jig image may be generated.

In some embodiments, a physical patient specific jig is manufactured based on the control data. The reduction tool image may comprise a bone facing surface image having a shape that corresponds to a shape of the reduced bone surface image at the installation position of the reduction tool image. The patient specific jig image may comprise a bone facing surface image having a shape that corresponds to a shape of the reduced bone surface image proximate the installation position of the reduction tool image. The patient specific jig image may comprise a reduction tool facing surface image shaped to receive a reduction tool in a predetermined orientation.

In some embodiments, the reduction tool image may include an aperture image there though, the aperture image shaped to receive a fastener for coupling the reduction tool to the reduced bone surface image. The patient specific jig image may comprise a reduction tool coupling image shaped to releasably couple the patient specific jig image to the reduction tool image.

The reduction tool image may comprise a reduction tool body having an outer perimeter. The patient specific jig image may comprise an outer perimeter, a first portion of the outer perimeter of the patient specific jig image may be shaped to match a first portion of the outer perimeter of the reduction tool body. The bone facing surface may extend at least 25% of the way around the bone surface image.

Forming a reduced bone surface image of the fractured bone structure of the patient may comprise forming a surface image of a corresponding contralateral bone of the patient. Forming a reduced bone surface image of the fractured bone structure of the patient may comprise reducing the fractured bone surface image to form the reduced bone surface.

A device for reducing a fractured bone is disclosed. The device may comprise a body having a bone facing surface shaped to match a shape of a surface of a reduced fractured bone at a location proximate a reduction tool installation position. The device may also include a reduction tool alignment member extending from the body and having a surface shaped to receive a reduction tool in a predetermined orientation.

The reduction tool may include an aperture therethough, the aperture may be shaped to receive a fastener for coupling the reduction tool to the reduced bone. The patient specific jig may comprise a reduction tool coupling shaped to releasably couple the patient specific jig to the reduction tool.

The reduction tool may comprise a reduction tool body having an outer perimeter. The patient specific jig may comprise an outer perimeter. A first portion of the outer perimeter of the patient specific jig may be shaped to match a first portion of the outer perimeter of the reduction tool body.

A device for fixing a fractured bone is disclosed. The device may comprise a body extending between a proximal end and a distal end. The body may have a patient specific surface shaped to match the surface of a reduced fractured bone of a patient according to three dimensional surface image data of the bone. A proximal arm may extend from the proximal end of the body and including a first implant alignment structure at a distal end of the arm. The first implant alignment structure may have a surface shaped to correspond to the shape of a first portion of an implant in a final position and orientation according to a pre-operatively planned position. A distal arm may extend from the distal end of the body and may include a second implant alignment structure at a distal end of the arm. The second implant alignment structure may have a surface shaped to correspond to the shape of a second portion of an implant in a final position and orientation according to a pre-operatively planned position.

The first implant alignment structure may be an open alignment structure having an alignment surface shaped to correspond with the shape of a sidewall of the first portion of the implant. The second implant alignment structure may be a closed alignment structure and may have an alignment surface shaped to correspond with the shape of a sidewall and outward facing surface of the second portion of the implant. The first alignment structure may include a finger that is shaped to extend into an aperture of an implant in a final installation position.

A device for fixing a fractured bone is disclosed. The device may comprise a body extending between a bone facing surface and an outward facing surface. The bone facing surface may be shaped to match the surface of a bone of a patient according to three dimensional surface image data of the bone. The device may also include an implant guide structure extending from the outward facing surface and may include an aperture that extends between the bone facing surface and a distal end of the implant guide structure. The aperture may be positioned and oriented to correspond with a position of an implant according to three-dimensional data of a preoperative plan. The device may also include an edge shaped to mate with the edge formed between three-dimensional data corresponding to the articular surface and the medial malleolus of the tibia of the patient. A plurality of anatomic structures may extend from the body. The anatomic structures may have a patient specific bone facing surface that may be shaped to match three-dimensional data corresponding to a bone surface image of a reduced fractured bone. The patient specific bone facing surface of one of the plurality of anatomic structures may extend form the body and may have a shape that corresponds to a shape of a surface of one of a head, a shaft, and a greater tuberosity of the bone of the patient.

A method of reducing a fractured bone of a patient is also disclosed. The method may include generating a fractured bone surface image from image data of the fractured bone structure of the patient, generating a reduced bone surface image from the image data of the fractured bone structure of the patient, generating a bone reduction tool image superimposed in an installation position on the reduced bone surface image, generating a patient specific jig image superimposed proximate the bone reduction tool image and the bone image according to the installation position of the bone reduction tool, and generating control data from the patient specific jig image.

A device for reducing a fractured bone is disclosed. The device may include a body having a bone facing surface shaped to match a shape of a surface of a reduced fractured bone at a location proximate a reduction tool installation position and a reduction tool alignment member extending from the body and having a surface shaped to receive a reduction tool in a predetermined orientation.

A device for reducing a fractured bone is disclosed. The device may include a body extending between a proximal end and a distal end, the body having a patient specific surface shaped to match the surface of a reduced fractured bone of a patient according to three dimensional surface image data of the bone. The device may also include a proximal arm extending from the proximal end of the body and including a first implant alignment structure at a distal end of the arm, the first implant alignment structure having a surface shaped to correspond to the shape of a first portion of an implant in a final position and orientation according to a pre-operatively planned position. The device may also include a distal arm extending from the distal end of the body and including a second implant alignment structure at a distal end of the arm, the second implant alignment structure having a surface shaped to correspond to the shape of a second portion of an implant in a final position and orientation according to a pre-operatively planned position.

A device for fixing a fractured bone is disclosed. The device may include a body extending between a bone facing surface and an outward facing surface, the bone facing surface shaped to match the surface of bone of a patient according to three dimensional surface image data of the bone and an implant guide structure extending from the outward facing surface and includes an aperture that extends between the bone facing surface and a distal end of the implant guide structure, the aperture being positioned and oriented to correspond with a position of an implant according to three-dimensional data of a preoperative plan.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

The present disclosure pertains to patient-specific bone fracture repair systems, devices, and methods for designing, manufacturing, and using such devices for achieving accurate bone reduction and repair and implant placement during surgery based on computer generated imaging of a particular patient. In preparation for fracture repair surgery, a variety of diagnostic images of the patient may be obtained utilizing CT, MRI, and other scans, such as x-rays, to generate three-dimensional (3-D) models of the patient's bone structure. From such 3-D models, the surgeon may determine the extent of the fracture and the specific installation location and orientation of one or more implants to be secured to the patient's fractured bone during surgery. Once the final location and orientation of the implants is determined, the surgeon may create a patient-specific jig for aiding in reducing the fracture or for installing a fixation implant on or in the patient's bone during the surgery.

The patient-specific jig may be designed and manufactured based on a patient-specific bone surface data. The patient-specific jig can be developed as either physical components via a prototyping machine or visual representations in a 3-D modeling software program based upon the 3-D images of the patient.

The methods and systems disclosed herein are based at least in part on pre-operating (preoperative) imaging and at least in part on orthopedic surgical procedures based upon the preoperative methods and systems. Preoperative imaging has a number of different purposes and generally is performed to help guide the surgeon during the surgical procedure, to allow for patient-specific tools or implants to be formed, etc. The present disclosure may be part of a system for designing and constructing one or more patient-specific jigs for use in an orthopedic surgical procedure in which a fixation implant is prepared, oriented, and implanted.

The referenced systems and methods are now described with reference to the accompanying drawings, in which one or more illustrated embodiments or arrangements of the systems and methods are shown in accordance with one or more embodiments disclosed herein. Aspects of the present systems and methods can take the form of an entirely hardware embodiment, an entirely software embodiment (including firmware, resident software, micro-code, etc.), or an embodiment combining software and hardware. One of skill in the art can appreciate that a software process can be transformed into an equivalent hardware structure, and a hardware structure can itself be transformed into an equivalent software process. Thus, the selection of a hardware implementation versus a software implementation is one of design choice, and is left to the implementer.

Figure 1:
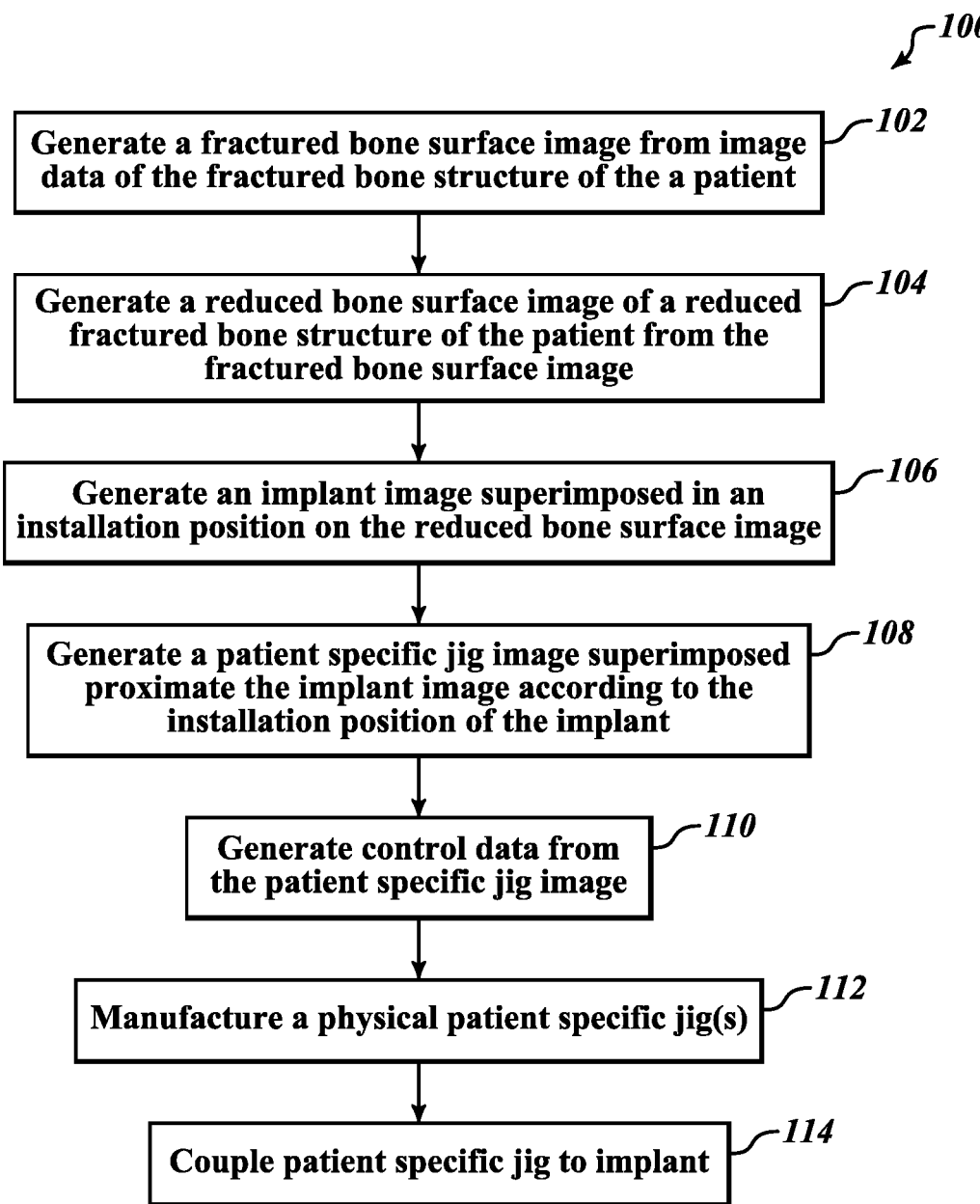
FIG. 1 depicts a method according to one or more embodiments disclosed herein.
Figure 2:
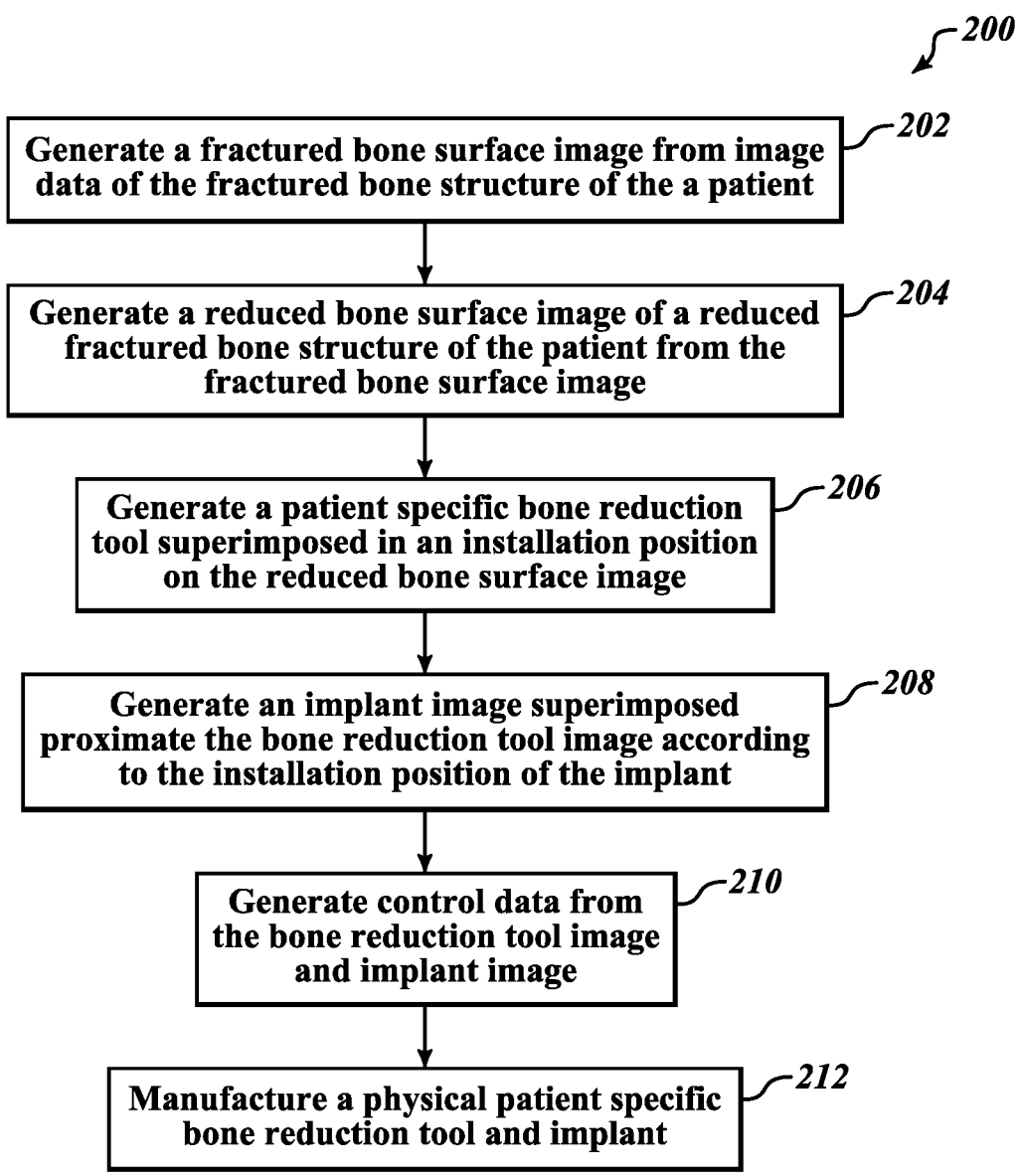
FIG. 2 depicts a method according to one or more embodiments disclosed herein.
Figure 3:
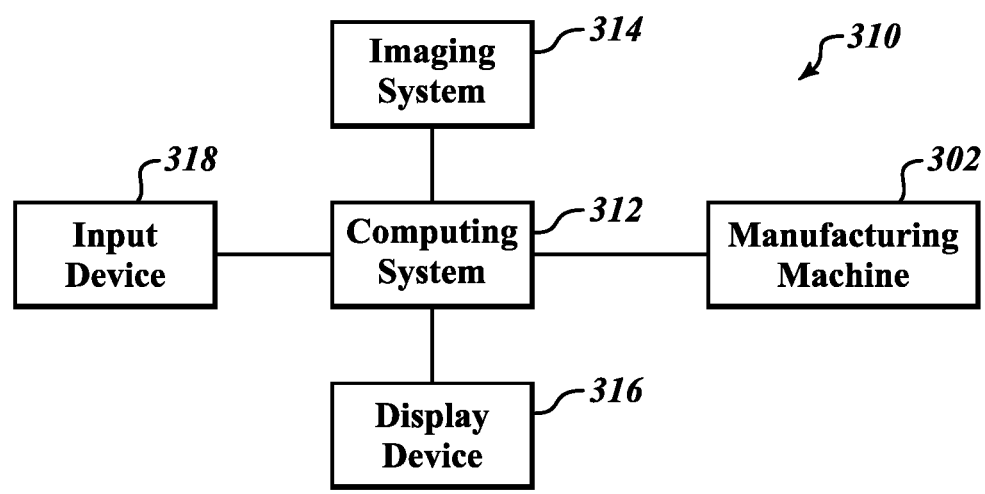
FIG. 3 depicts a system according to one or more embodiments disclosed herein.

FIGS. 1 and 2 are flow diagrams illustrating a method pertaining to preoperative imaging and planning according to aspects of the present disclosure. FIG. 3 shows a system for carrying out the methods of the present disclosure, such as that described with reference to FIGS. 1 and 2. FIG. 3 shows a simplified system 310 of devices that may be used to carry out the methods of the present disclosure. The system 310 comprises a computing system 312 coupled to an imaging system 314. The imaging system 314 captures patient image data and transfers the data to the computing system 312. The computing system 312 processes such data and transmits the data to a display device 316 for display of images and other data. An input device 318 receives input from a computer or an operator (such as a surgeon) and transmits inputted information to the computing system 312 for processing. Such input devices 318 are well known in the art and will not be described in greater detail. The imaging system 314 may include a bone imaging machine for forming three-dimensional image data from a bone structure of a patient. The computing system 312 may include a patient-specific device generator for processing and generating images, and a patient-specific device converter for generating design control data. A manufacturing machine 320 receives the control data from the computing system 312 for making devices described herein, including patient-specific jigs.

Figure 6A:
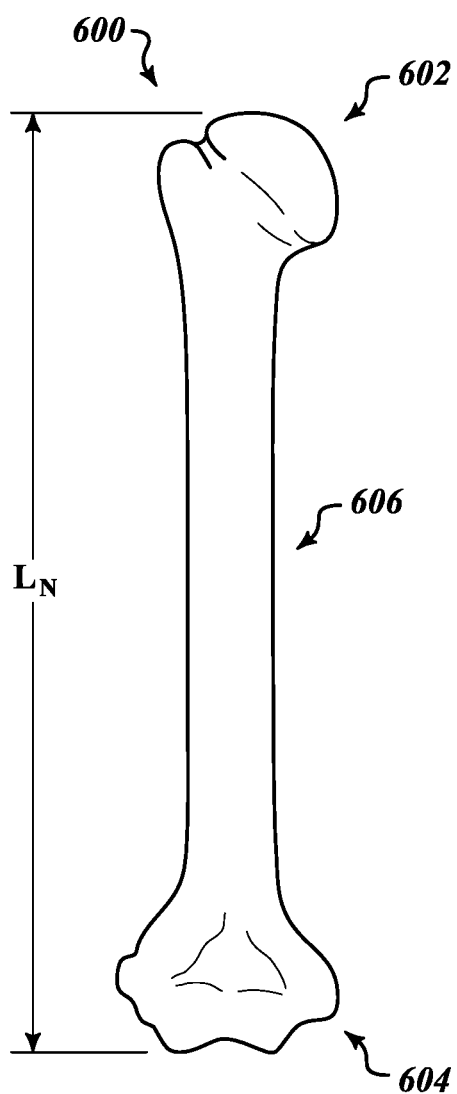
FIGS. 6A and 6B depict a front view of a left and right humerus bones, respectively, according to one or more embodiments disclosed herein.
Figure 6B:
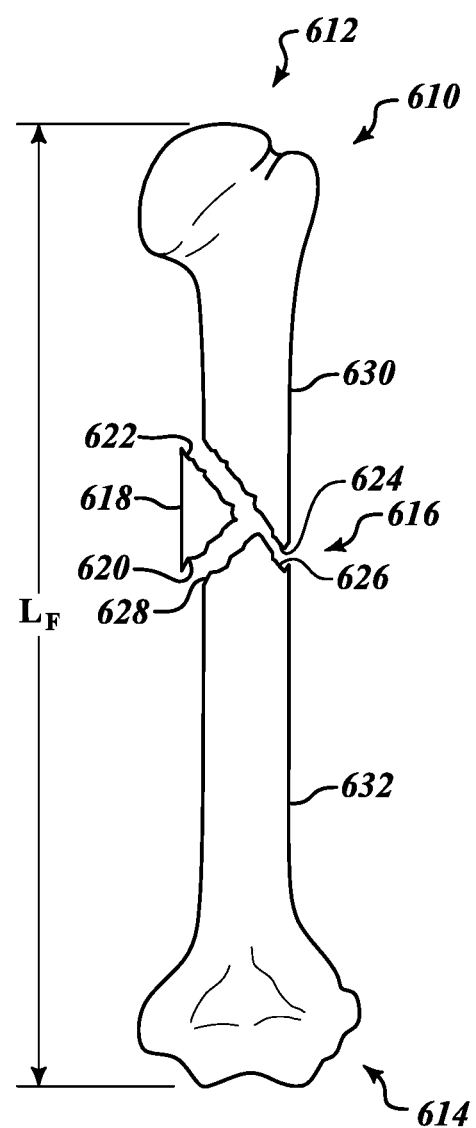
Figure 7A:
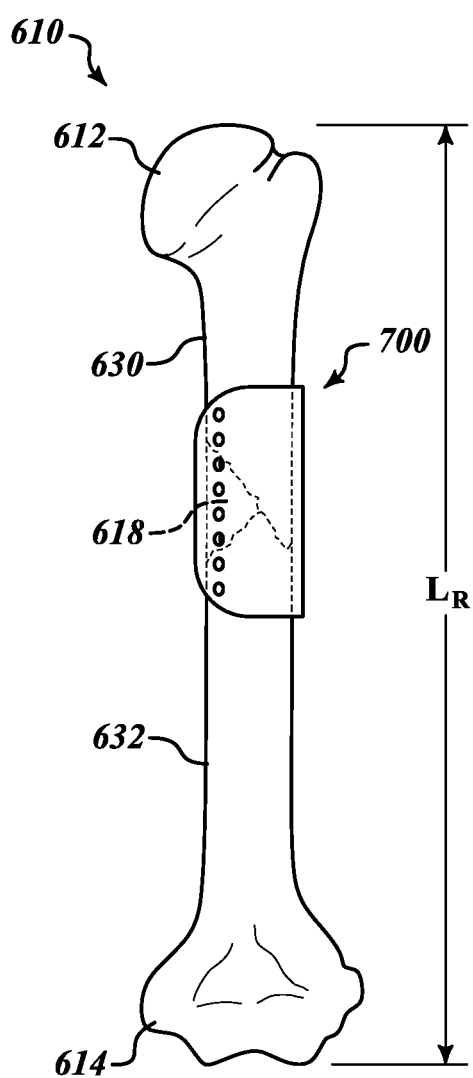
FIG. 7A depicts a front view of a humerus with a reduced fracture and an installed patient specific jig according to one or more embodiments disclosed herein.

In FIG. 1, a method 100 according to an embodiment may start at block 102. At block 102, a bone imaging machine generates a bone surface image from three-dimensional image data from the fractured bone structure of a patient, for example, as shown in FIGS. 6A and 6B. At block 104, a reduced bone surface image of a reduced fractured bone structure of the patient is generated from the fractured bone surface image, for example, as shown in FIG. 7A. In some embodiments, the three-dimensional image data of the fractured bone structure of a patient may include three-dimensional models of one or more portions of the fractured bone of the patient. In some embodiments, the individual three-dimensional models of the portions of the fractured bone are manipulated and placed in a reduced configuration such that the reduced bone surface image represents a pre-operatively planned reduction of the fractured bone. The pre-operatively planned reduction represents that planned actual reduction of the patient's actual fractured bone.

In some embodiments, bone surface images may be made of a patients corresponding unfractured or healthy bone to aid in determining the reduced bone surface image of the reduced fractured bone structure. For example, in some embodiments, such as that shown in FIGS. 6A and 6B, a right tibia may be fractured, while a left tibia is unfractured. In such embodiments, imaging, such as an x-ray image, may be used to determine the length LN of the left tibia. The lengths of a person's left and right bones, in the embodiments, the left tibia and right tibia, are known to be similar Thus, the reduced bone surface image of the right tibia may be formed such that the length LF of the reduced fractured right bone corresponds to the length LN of the unfractured left tibia. By corresponding, the lengths are the same or similar to each other.

At block 106, a patient-specific device generator generates an implant image superimposed in an installation position on the reduced bone surface image. The implant image is positioned in its final, implanted position and orientation, regardless of the state of the patient's bone in the bone surface image. The implant image may be a patient specific implant image, having a surface that is shaped to match or otherwise mate with the bone surface image of the patient. A patient specific implant formed based on the implant image may have an actual surface that matches or otherwise mates with the reduced fractured bone of the patient.

At block 108, the patient-specific device generator generates a patient specific jig image superimposed proximate the reduced bone surface image and the implant image according to the installation position of the implant. The patient-specific device generator may use the bone surface image to create a patient-specific device with anatomic engagement members that have an engagement surface that corresponds to, matches, or is the negative contour of the patient's anatomy. In some embodiments, the engagement surface is shaped to nestingly mate with the corresponding surface of the bone of the patient. The patient-specific device generator may use the implant image to generate implant engagement members that engage with features of the implant, such as a surface, end, or aperture of the implant. The patient-specific device generator may also use the implant image and the bone surface image to generate jig alignment features or members.

At block 110, a patient-specific device converter generates control data from the patient-specific jig image. The control data may be used by a machine during a manufacturing process to create physical patient-specific jigs by additive or subtractive machining, such as fused deposition modeling, stereolithography, or other methods. At block 112, the manufacturing device creates a physical patient-specific jig.

At block 114, the implant may by coupled to the patient specific jig. Coupling the patient specific jig and the implant together may provide for greater ease of handling, transportation, and use as compared to uncoupled implants and jigs.

In FIG. 2, a method 200 according to an embodiment may start at block 202. At block 202, a bone imaging machine generates a bone surface image from three-dimensional image data from the fractured bone structure of a patient, for example, as shown in FIGS. 6A and 6B. At block 204, a reduced bone surface image of a reduced fractured bone structure of the patient is generated from the fractured bone surface image, for example, as shown in FIG. 7A. In some embodiments, the three-dimensional image data of the fractured bone structure of a patient may include three-dimensional models of one or more portions of the fractured bone of the patient. In some embodiments, the individual three-dimensional models of the portions of the fractured bone are manipulated and placed in a reduced configuration such that the reduced bone surface image represents a pre-operatively planned reduction of the fractured bone. The pre-operatively planned reduction represents that planned actual reduction of the patient's actual fractured bone.

In some embodiments, bone surface images may be made of a patients corresponding unfractured or healthy bone to aid in determining the reduced bone surface image of the reduced fractured bone structure. For example, in some embodiments, a right tibia may be fractured, while a left tibia is unfractured. In such embodiments, imaging, such as an x-ray image, may be used to determine the length LN of the left tibia. The lengths of a person's left and right bones, in the embodiments, the left tibia and right tibia, are known to have similar lengths. Thus, the reduced bone surface image of the right tibia may be formed such that the length LF of the reduced fractured right bone corresponds to the length LN of the unfractured left tibia. By corresponding, the lengths are the same or similar to each other.

At block 206, a patient-specific device generator generates a bone reduction tool image superimposed in an installation position on the reduced bone surface image. The bone reduction tool image is positioned in its final position and orientation, regardless of the state of the patient's bone in the bone surface image. The bone reduction tool image may be a patient specific image, having a surface that is shaped to match or otherwise mate with the bone surface image of the patient. A patient specific bone reduction tool formed based on the implant image may have an actual surface that matches or otherwise mates with the reduced fractured bone of the patient.

At block 208, the patient-specific device generator generates an implant image superimposed proximate the reduced bone surface image and the bone reduction tool image according to the installation position of the implant. The patient-specific device generator may use the bone surface image to create a patient-specific device with anatomic engagement members that have an engagement surface that corresponds to, matches, or is the negative contour of the patient's anatomy. In some embodiments, the engagement surface is shaped to nestingly mate with the corresponding surface of the bone of the patient. The patient-specific device generator may use the implant image to generate implant engagement members that engage with features of the implant, such as a surface, end, or aperture of the implant. The patient-specific device generator may also use the implant image and the bone surface image to generate jig alignment features or members.

Figure 7B:
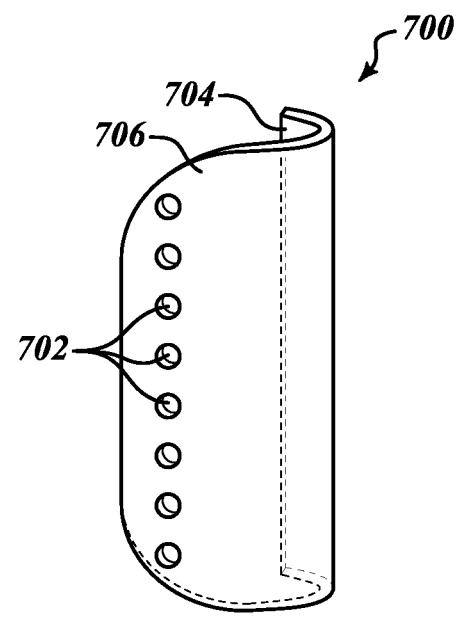
FIG. 7B shows a front view of the patient specific jig of FIG. 7A.
Figure 7C:
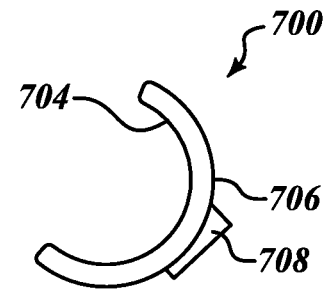
FIG. 7C shows a top view of the patient specific jig of FIG. 7A.

In some embodiments, the bone reduction tool may be an implant. For example, as shown in FIGS. 7A-7C, the bone reduction tool includes apertures for receiving fasteners to fasten the bone reduction tool to the patient's bone. It is contemplated that the bone reduction tool and the other implants and tools disclosed herein may be any standard or patient-specific tool or implant.

At block 210, a patient-specific device converter generates control data from the bone reduction tool image and the implant image. The control data may be used by a machine during a manufacturing process to create physical bone reduction tools and the implants by additive or subtractive machining, such as fused deposition modeling, stereo lithography, or other methods. At block 212, the manufacturing device creates a physical bone reduction tool and the implant.

As discussed above, FIG. 3 shows the system 310 for carrying out the methods of FIGS. 1 and 2 according to some aspects of the present disclosure. The computing system 312 may include instructions in the form of computer software for automatically generating images of implants in final installation positions on the bone structure images. In some aspects, a surgeon input information into the input device 318 for creating or altering jig images or implant images for a particular patient based on the surgeon's understanding of the particular bone structure of the patient as displayed on the display device 316 during preoperative planning.

Figure 4:
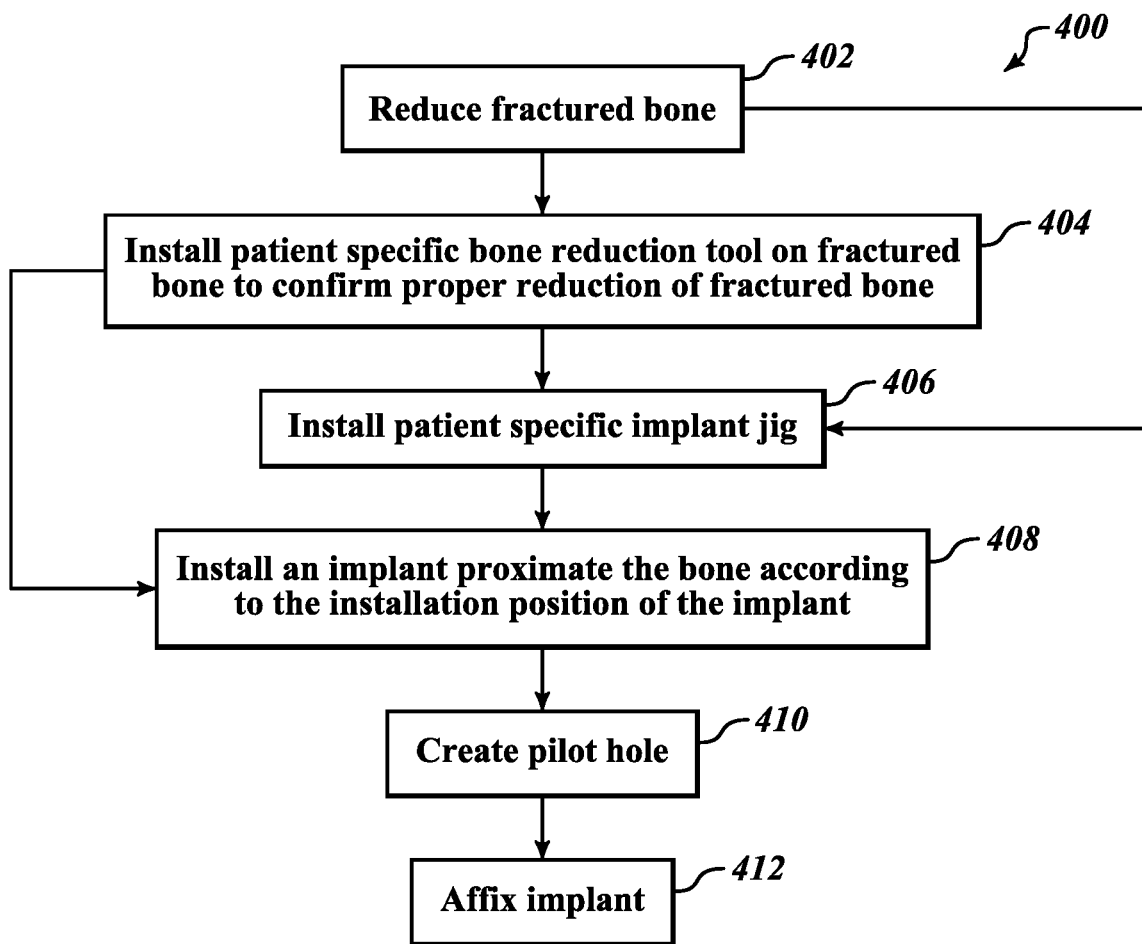
FIG. 4 depicts a method according to one or more embodiments disclosed herein.
Figure 5:
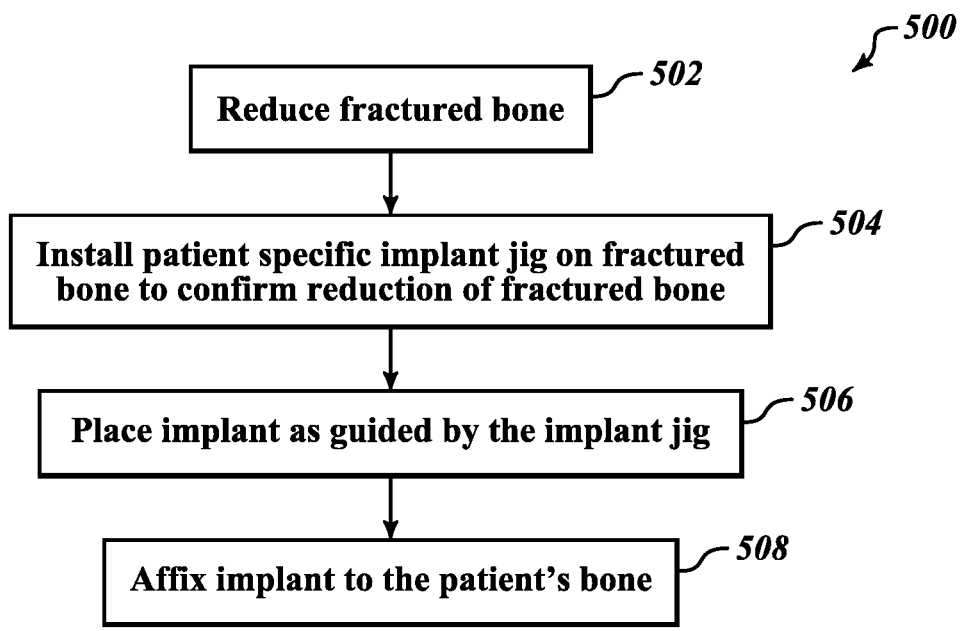
FIG. 5 depicts a method according to one or more embodiments disclosed herein.

FIGS. 4 and 5 are flow diagrams of methods pertaining to operative surgery according to aspects of the present disclosure. The methods of FIGS. 4 and 5 may be carried out by a surgeon or by a machine, or by both. Moreover, the process may utilize some or all of the devices discussed with reference to FIGS. 1 2, and 3 during surgery, such as viewing the preoperative images displayed on the display device while operating on a patient.

In FIG. 4, a method 400 according to an embodiment disclosed herein may start at block 402. The method 400 may be carried out using patient specific devices, such as, for example, shown in FIGS. 7-12. In many fracture procedures, a first step may be to reduce the fractured bone. Reduction may include, for example, repositioning one or more portions of the fractured bone relative to each other such that they are positioned in their original, pre-fractured, location. In a simple fracture, a bone breaks cleanly in two pieces and reduction may include aligning the fractured surface of each of the two pieces with each other such that the faces mate with each other. In a comminuted fracture the bone is broken into more than two pieces. Reducing a comminuted fracture may include aligning broken pieces such that their fractured surfaces are aligned and mated with each other and the broken pieces of bone are placed such that the bone is restructured back to the shape of a normal anatomy, such as a pre-fractured shape.

At block 404, a doctor or machine may place a patient specific bone reduction tool on the reduced bone of the patient, the patient specific bone reduction tool formed according to a predetermined reduction of the bone based on three-dimensional image data from the bone structure of a patient. Placing the patient specific bone reduction tool may include aligning an anatomical alignment surface of the tool with pre-selected areas at, adjacent, or peripheral fractured location of bone. For example, after reducing the bone, the doctor may place the patient specific bone reduction tool on the reduced bone structure and, based on the degree of alignment between the tool and the bone, determine whether the bone is properly reduced or wither further reduction or manipulation of the fractured bone should be conducted. By positioning the jig in such a manner, the doctor may evaluate the position of the reduced bone fragments and may make adjustments to the fragments before attempting to place an implant in its final, predetermined, installation position.

At block 406, a doctor or machine may install a patient specific implant guide jig proximate the fracture location on the bone of the patient. The implant guide jig includes a patient specific surface that that corresponds to, matches, or is the negative contour of the patient's anatomy. In some embodiments, the patient specific surface is shaped to nestingly mate with the corresponding surface of the bone of the patient.

At block 408, a doctor or machine may install an implant proximate the bone according to the installation position of the implant. The installation of the implant may be guided by implant alignment surfaces of the patient specific implant guide jig that aid in aligning the implant in the proper position and orientation on the patient's bone.

If the implant has been placed in the correct final installation position, the patient specific surface of the patient specific jig should engage with the corresponding to preselected areas adjacent or peripheral the installation position of the implant on the bone of the patient, and the implant alignment surfaces should engage with the implant. Thus, at block 408, a doctor or machine may inspect the alignment and engagement of the alignment surfaces and determine whether the anatomical patient specific surface of the patient specific jig is engaged to the pre-selected areas adjacent or peripheral the fractured bone of the patient, and the implant alignment surface is engaged with the implant. If the surfaces are properly engaged, then the implant is installed in the correct installation position and orientation. If the alignment members are not properly engaged, then the implant is not in the correct final installation position.

Furthermore, an evaluation of the alignment of the surfaces relative to the patient's anatomy or the implant may help quantify displacement of the current position of the implant with the final installation position of the implant.

At block 410, a doctor or machine may create pilot holes in the patient's bone and at block 412, a doctor or machine may affix the implant to the patient's bone, for example, using fasteners, such as screws.

In some embodiments, one or more of the blocks of method 400 may be omitted. For example, in some embodiments the method may proceed to block 406, from block 402 without carrying out block 404. In other embodiments, the method 400 may proceed to block 408, from block 404 without carrying out block 406.

In FIG. 5, a method 500 according to an embodiment disclosed herein may start at block 502. The method 500 may be carried out using patient specific devices, such as, for example, shown in FIGS. 7-12. In many fracture procedures, the first step is to reduce the fractured bone. Reduction may include, for example, repositioning one or more portions of the fractured bone into relative to each other to such that they are positioned in their original, pre-fractured, location.

At block 504, a doctor or machine may place a patient specific implant guide jig on the reduced bone of the patient, the patient specific bone reduction tool formed according to a predetermined reduction of the bone based on three-dimensional image data from the bone structure of a patient. Placing the patient specific bone reduction tool may include aligning an anatomical alignment surface of the tool with pre-selected areas at, adjacent, or peripheral fractured location of bone. For example, after reducing the bone, the doctor may place the patient specific bone reduction tool on the reduced bone structure and based on the degree of alignment between the tool and the bone, determine whether the bone is properly reduced or wither further reduction or manipulation of the fractured bone should be conducted. By positioning the jig in such a manner, the doctor may evaluate the position of the reduced bone fragments and may make adjustments to the fragments before attempting to place an implant in its final or predetermined installation position.

The implant guide jig includes a patient specific surface that that corresponds to, matches, or is the negative contour of the patient's anatomy. In some embodiments, the patient specific surface is shaped to nestingly mate with the corresponding surface of the bone of the patient.

At block 506, a doctor or machine may install an implant proximate the bone according to the installation position of the implant. The installation of the implant may be guided by implant alignment surfaces of the patient specific implant guide jig that aid is aligning the implant in the proper position and orientation on the patient's bone.

If the implant has been placed in the correct final installation position, the patient specific surface of the patient specific jig should engage with the corresponding pre-selected areas adjacent or peripheral to the implant installation position on the bone of the patient, and the implant alignment surfaces should engage with the implant. Thus, at block 506, a doctor or machine may inspect the alignment and engagement of the alignment surfaces and determine whether the anatomical patient specific surface of the patient specific jig is engaged to the pre-selected areas adjacent or peripheral the fractured bone of the patient, and the implant alignment surface is engaged with the implant. If the surfaces are properly engaged, then the implant is installed in the correct installation position and orientation. If the alignment members are not properly engaged, then the implant is not in the correct final installation position.

Furthermore, an evaluation of the alignment of the surfaces relative to the patient's anatomy or the implant may help quantify displacement of the current position of the implant with the final installation position of the implant.

At block 508, a doctor or machine may affix the implant to the patient's bone, for example, using fasteners, such as screws.

FIGS. 6A and 6B depict a healthy left humerus 600 and a fractured right humerous 610, respectively. The healthy left humerus 600 includes a shaft or body 606 extending between a proximal end 602, including the head, and a distal end 604. The length of the healthy left humerus 600, as measured between the proximal end 602 and distal end 604 is LN.

The right fractured humerus 610 includes a shaft or body 616 extending between a proximal end 612, including the head, and a distal end 614. The length of the healthy left humerus 610, as measured between the proximal end 612 and distal end 614 is LF. The fractured bone 610 includes three pieces, a proximal portion 630, a distal portion 632, and a fragment 618. The fracture depicted in FIG. 6B is a three piece comminuted bone fracture. In other embodiments, other types of fractures may occur. In some embodiments, a fracture may include two pieces or more than three pieces. In some embodiments, the bone surface image of the contralateral unfractured bone image may be used as a model of the bone surface image of the reduced fractured bone such that the doctor reduces the fractured bone surface image such that it matches the unfractured bone image, in some embodiments, the reduced image may match an inverse or mirrored unfractured bone image.

When reducing the bone fracture depicted in FIG. 6B, a doctor attempts to close the gaps in between the pieces of bone 630, 632, and 634 by moving the pieces of bone 630, 632, and 634 into their pre fracture orientations and positions. For example, a doctor may align the fracture surface 624 of bone piece 630 with the fracture surface 626 of bone piece 632 and fracture surface 622 of bone piece 618 and to also align the fracture surface 628 of bone piece 632 with the fracture surface 620 of bone piece 618 such that the respective surfaces are mated with each other. For example, surface 624 is mated with fracture surface 626 and fracture surface 622 while fracture surface 628 is mated with the fracture surface 620.

An improperly reduced bone fracture may result in one extremity, such as an arm or leg, being longer or shorter than the opposite extremity. For example a fractured left femur may be reduced and heal such that the healed left femur is longer than the health right femur. Such differences in lengths can cause problems in patients because one leg may receive greater loads when walking and other parts of the body may adjust to compensate for the different lengths, causing pelvis and back problems. Therefore, a doctor may measure the length of a corresponding healthy bone and use that length to aid in properly reducing the fractured bone.

In some embodiments, some portions of a fractured bone may not be useable when reducing the fracture. For example, pieces of the bone may be missing, too small, or too damaged such that the doctor cannot put them in their proper place when reducing the bone fracture. This may lead to the bone being reduced such that its length is not correct or with bone pieces in an incorrect position or orientation.

FIGS. 7A, 7B, and 7C depict a reduced fractured bone 610 and a bone reduction tool 700. In some embodiments, FIGS. 7A, 7B, and 7C depict a reduced fractured bone image and a bone reduction tool image. As shown in FIG. 7A, the bone reduction tool 700 is shown proximate to the fracture of the bone of the patient.

The bone reduction tool 700 has several features and uses including aiding in reducing the bone fracture and in fixing the fractured bone. For example, during the fracture reduction process the bone portions of the fractured bone 630, 618, and 632 are repositioned such that the fracture surfaces of the respective portions of fractured bone 630, 618, and 632 mate with each other and the bone 610 is reduced to a pre-fracture configuration. In the preoperative planning stages of the surgery, a reduced bone image is formed based on the surface images of the portions of the fractured bone 630, 618, and 632 and other factors, such as the unfractured length of the bone or an unfractured length of a corresponding bone of a patient.

When the bone images are reduced, the bone image may have a unique surface shape. The bone reduction tool 700 includes a bone facing surface 704 that includes one or more portions that are shaped to match respective portions of unique surface shape of the reduced bone. For example, as shown in FIGS. 7A, 7B, and 7C, the bone facing surface 704 of the body of the bone reduction tool 700 spans the fracture such that is makes contact with each of the portions of the fractured bone 630, 618, and 632.

The bone facing surface 704 is an anatomic alignment surface shaped to match the surface of the reduced fractured bone 610 in a single position and orientation. The shape and contours of the bone facing surface 704 may be determined based upon the 3-D modeling images of the patient, a combination of two-dimensional radiographic images of the patient, or a combination of three-dimensional and two-dimensional images of a patient. The shape of the bone facing surface 704 is sometimes referred to as a negative of the anatomic structure with which the bone facing surface 704 aligns or engages. It is a negative because, for example, a protrusion on the anatomic surface structure of the bone surface image of the bone 610 corresponds to a depression on bone facing surface 704 while a depression on the anatomic surface structure of the bone surface image of the bone 610 corresponds to a protrusion on the bone facing surface 704.

During the fracture reduction process, a reduction clamp may be used to hold the reduced portions of bone in place. As shown in FIG. 7C, the bone reduction tool 700 includes an outward facing surface 706 that is on an opposite side of the body of the bone reduction tool 700 from the bone facing surface 704. The outward facing surface may include a clamp receiving surface 708 that is shaped to receive a portion of a bone reduction clamp. For example, the clamp receiving surface 708 is a planar surface shaped such that is provides a stable, planar surface for a first jaw of a clamp to exert a reduction force onto the fractured bone. A second jaw of a clamp may exert a reduction force directly onto the bone of the patient at a location opposite the clamp receiving surface 708.

A doctor may use a bone reduction tool, such as the bone reduction tool 700, during a fracture repair. For example, after the patient's bone fracture, the doctor may attempt to place the bone reduction tool 700 in its preoperatively planned installation position and orientation. When placing the bone reduction tool 700, the doctor attempts to align or engage the patient specific surface 704 with the anatomic structure of the patient and then observe the alignment or misalignment of the patient specific surface 704 with the portions of fractured bone 618, 630, and 632. The alignment or misalignment of the prosthetic alignment surfaces with patient specific surface 704 with the portions of fractured bone 618, 630, and 632 indicates information to the doctor regarding the reduction of the bone fracture. For example, if the patient specific surface 704 aligns with the surface of the portions of fractured bone 618, 630, and 632, then a doctor may know that the bone 601 has been properly reduced, while misaligned alignment of the surfaces may indicate how the position or orientation of one or more of the portions of fractured bone 618, 630, and 632 should be changed to reduce the bone into the final pre-operatively planned reduced position.

The bone reduction tool 700 may also include apertures 702 that extend between the bone facing surface 704 and the outward facing surface 706. The apertures 702 may be pilot hole guide apertures. As pilot hole guide apertures, the apertures 702 aid in the drilling of pilot holes for use in affixing an implant to the bone of the patient. For example, after the bone 610 is reduced, an implant, (see, e.g., implant 850 in FIG. 8A) may be affixed to the portions of fractured bone 618, 630, and 632 to hold the portions of fractured bone 618, 630, and 632 in place while the bone 610 heals. Fasteners, such as screws may be used to affix the implant to the bone 610. By drilling the pilot holes into the portions of fractured bone 618, 630, and 632 while the bone reduction tool 700 holds the portions of fractured bone 618, 630, and 632 in place, the doctor may ensure that the pilot holes are in the proper location. For example, the apertures 702 may be formed such that they correspond to the location of an aperture 852 of the implant 850 when the implant 850 and the portions of fractured bone 618, 630, and 632 are in the proper pre-operatively planned position. Thus, after the doctor uses the bone reduction tool 700 and its apertures 702 to form the pilot holes, the doctor may remove the bone reduction tool 700 and then used the pilot holes as a guide for affixing the implant to the portions of fractured bone 618, 630, and 632 in their pre-operatively planned position and orientation.

In some embodiments, the apertures 702 are shaped to receive fasteners, such as screws for affixing the bone reduction tool 700 to the reduced fractured bone of the patient. In such an embodiment, the bone reduction tool 700 is also an implant that holds the portions of fractured bone 618, 630, and 632 in place while the bone heals.

Figure 8A:
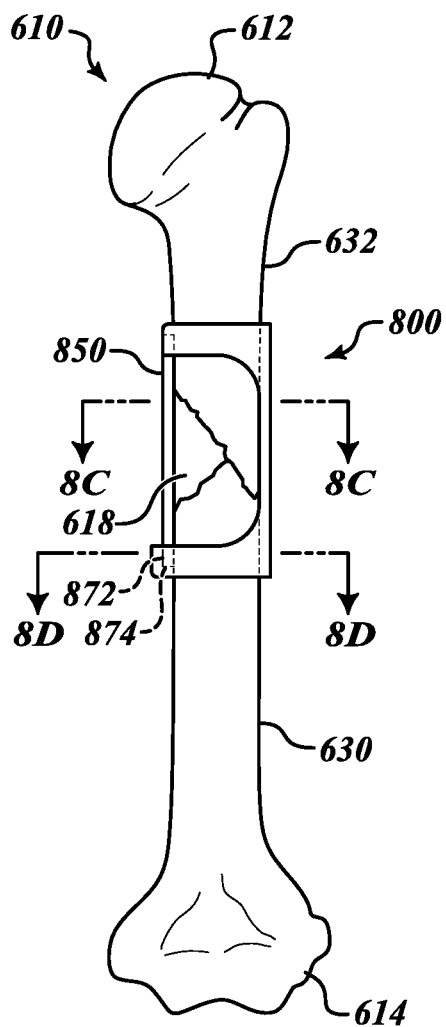
FIG. 8A depicts a front view of a humerus with a reduced fracture and an installed patient specific jig and implant according to one or more embodiments disclosed herein.
Figure 8B:
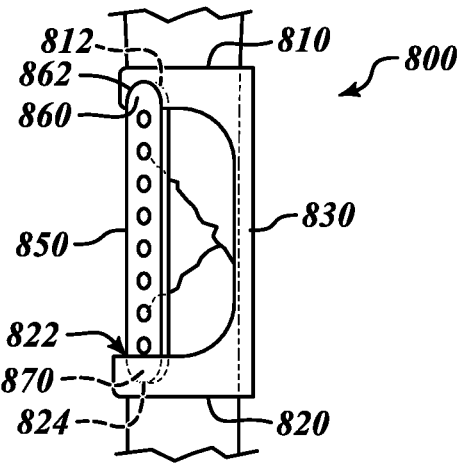
FIG. 8B shows a side view of the humerus with the reduced fracture and the installed patient specific jig and implant patient specific jig of FIG. 8A.
Figure 8C:
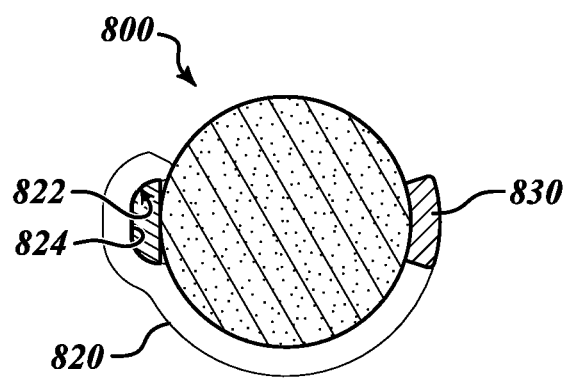
FIG. 8C shows a section view along 8C-8C of FIG. 8A.
Figure 8D:
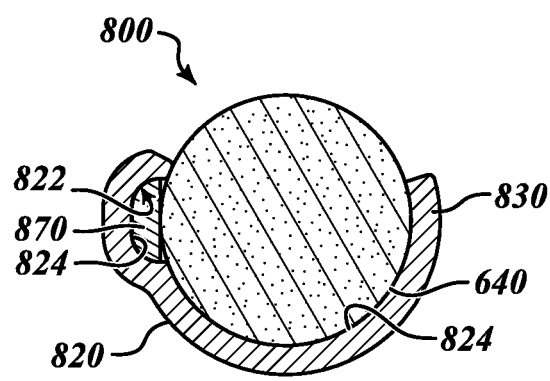
FIG. 8D shows a section view along 8D-8D of FIG. 8A.

FIGS. 8A, 8B, 8C, and 8D depict a bone reduction tool and implant alignment guide 800, which may be referred to as simply an implant alignment guide 800 or guide 800, along with an implant 850. The bone reduction tool and implant alignment guide 800 may be used as one or both of a bone reduction tool or implant alignment guide. The FIGS. 8A, 8B, 8C, and 7D depict a reduced fractured bone 610 with the bone reduction tool and implant alignment guide 800. In some embodiments, FIGS. 8A, 8B, 8C, and 7D depict a reduced fractured bone image and a bone reduction tool and implant alignment guide image. As shown in FIG. 8A, the guide 800 is shown proximate to the fracture of the bone of the patient and the implant 850. It is contemplated that the implant 850 and the other implants disclosed herein may be any standard or patient-specific implant.

The guide 800 has several features and uses, including aiding in reducing the bone fracture and in fixing the fractured bone. For example, during the fracture reduction process the bone portions of the fractured bone 630, 618, and 632 are repositioned such that the fracture surfaces of the respective portions of fractured bone 630, 618, and 632 mate with each other and the bone 610 is reduced to a pre-fracture configuration.

The guide 800 includes a main body 830 extending between proximal and distal ends thereof. Proximal arm 810 and distal arm 820 extend from respective ends of the main body 830. The main body 830, the proximal arm 810 and the distal arm 820 each include a respective portion of a bone facing surfaces 824 that each include one or more portions that are shaped to match respective portions of the surface of the reduced bone. For example, as shown in FIGS. 8A, 8B, 8C, and 8D the bone facing surfaces 824 of the body of the guide 800 spans the fracture such that is makes contact with each of the portions of the fractured bone 630, 618, and 632.

The bone facing surfaces 824 are anatomic alignment surfaces shaped to match the surface of the reduced fractured bone 610 in a single position and orientation. The shape and contours of the bone facing surfaces 824 may be determined based upon the 3-D modeling images of the patient, a combination of two-dimensional radiographic images of the patient, or a combination of three-dimensional and two-dimensional images of a patient. The shape of the bone facing surfaces 824 are sometimes referred to as a negative of the anatomic structure with which the bone facing surfaces 824 align or engage. It is a negative because, for example, a protrusion on the anatomic surface structure of the bone surface image of the bone 610 corresponds to a depression on the bone facing surfaces 824 while a depression on the anatomic surface structure of the bone surface image of the bone 610 corresponds to a protrusion on the bone facing surfaces 824.

During the fracture reduction process, a reduction clamp may be used to hold the reduced portions of bone in place. The guide may include an outward facing surface that is on an opposite side of the body of the guide 800 from the bone facing surfaces 824. The outward facing surface may include a clamp receiving surface that is shaped to receive a portion of a bone reduction clamp.

A doctor may use a bone reduction tool, such as the guide 800, during a fracture repair. For example, after the patient's bone fracture, the doctor may attempt to place the bone reduction tool 700 in its preoperatively planned installation position and orientation. When placing the guide 800, the doctor attempts to align or engage the patient specific bone facing surfaces 824 with the anatomic structure of the patient and then observe the alignment or misalignment of the patient specific bone facing surfaces 824 with the portions of fractured bone 618, 630, and 632. The alignment or misalignment of the prosthetic alignment surfaces with patient specific bone facing surfaces 824 with the portions of fractured bone 618, 630, and 632 indicates information to the doctor regarding the reduction of the bone fracture. For example, if the patient specific bone facing surfaces 824 aligns with the surface of the portions of fractured bone 618, 630, and 632, then a doctor may know that the bone 601 has been properly reduced, while misaligned alignment of the surfaces may indicate how the position or orientation of one or more of the portions of fractured bone 618, 630, and 632 should be changed to reduce the bone into the final pre-operatively planned reduced position.

The distal ends of the proximal arm 810 and distal arm 820 include implant alignment structures 812, 824 for aligning the implant 850 with the bone 610 of the patient in position and orientation determined based on preoperative planning. The implant alignment structures 812, 824 are alignment surfaces shaped to match the surface of the implant 850 in a single position and orientation. The shape and contours of the implant alignment structures 812, 824 may be determined based upon the bone surface 640 formed from the 3-D modeling images of the patient, a combination of two-dimensional radiographic images of the patient, or a combination of three-dimensional and two-dimensional images of a patient and a final position and orientation of the implant 850. For symmetrical implants, wherein the implant is symmetrical about one or more axis, the rotation or orientation of the implant about the axis of symmetry is still considered a single orientation. For example implant 850 is symmetrical such that rotating the implant 850 such that ends 860 and 870 are swapped would still result in the same orientation and position of the implant.

The alignment structure 812 at the distal end of the proximal arm 810 is an open alignment structure wherein the alignment surface 812 nestingly or otherwise mates with the outer perimeter surface 862 of the end 860 of the implant 850, but may not include roof structure with a surface that mates with an outward facing surface of the implant. In this way, the end of the implant may not be captured by the alignment structure 812.

The alignment structure 822 at the distal end of the distal arm 820 is a closed alignment structure wherein the alignment surface 824 nestingly or otherwise mates with the outer perimeter surface 872 of the end 870 of the implant 850 and also includes a surface on a roof structure of the arm 820 that mates with an outward facing surface 874 of the implant. In this way, the end of the implant 870 is captured by the alignment structure 822. In such an embodiment, the end of the implant 870 is inserted into a cavity formed by the alignment surface 824 of the distal arm 820.

Once the doctor has confirmed that the guide 800 or the implant is properly oriented and located, the doctor can affix the implant to the bone 610 of the patient, for example, by fastening the implant to the bone with screws or other fasteners.

Figure 9A:
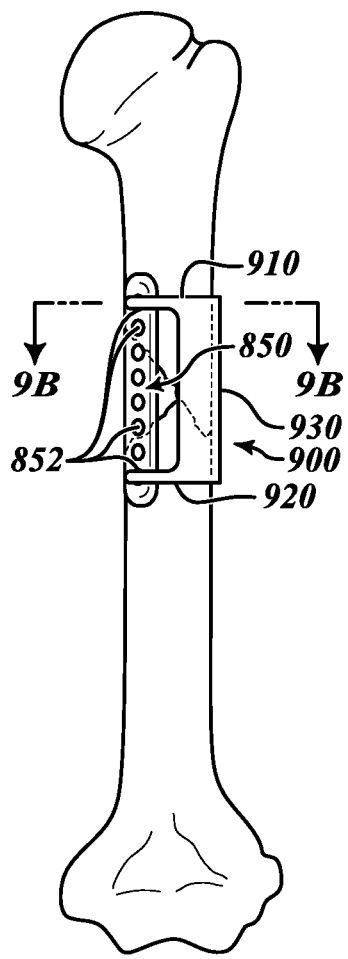
FIG. 9A depicts a front view of a humerus with a reduced fracture and an installed patient specific jig and implant according to one or more embodiments disclosed herein.
Figure 9B:
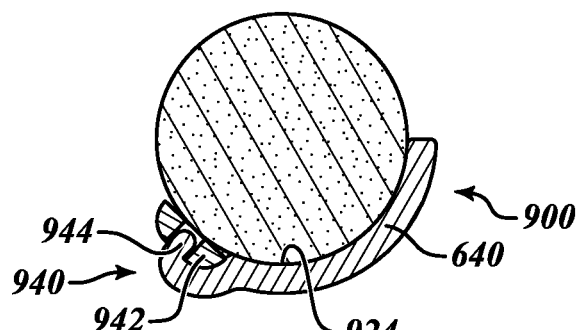
FIG. 9B shows a section view along 9B-9B of FIG. 9A.

FIGS. 9A and 9B depict a bone reduction tool and implant alignment guide 900, which may be referred to as simply an implant alignment guide or guide 900, along with the implant 850. The guide 900 may be used as one or both of a bone reduction tool or implant alignment guide. FIGS. 9A and 9B depict a reduced fractured bone 610 with the bone reduction tool and implant alignment guide 900. In some embodiments, FIGS. 9A and 9B depict a reduced fractured bone image and a bone reduction tool and implant alignment guide image. As shown in FIG. 9A, the guide 900 is shown proximate to the fracture of the bone of the patient and the implant 850.

The guide 900 has several features and uses, including aiding in reducing the bone fracture and in fixing the fractured bone. For example, during the fracture reduction process the bone portions of the fractured bone 630, 618, and 632 are repositioned such that the fracture surfaces of the respective portions of fractured bone 630, 618, and 632 mate with each other and the bone 610 is reduced to a pre-fracture configuration.

The guide 900 includes a main body 930 extending between proximal and distal ends thereof. Proximal arm 910 and distal arm 920 extend from respective ends of the main body 930. The main body 930, the proximal arm 910 and the distal arm 920 each include a respective portion of a bone facing surfaces 924 that each include one or more portions that are shaped to match respective portions of unique surface shape of the reduced bone. For example, as shown in FIGS. 9A and 9B the bone facing surfaces 924 of the body of the guide 900 spans the fracture such that is makes contact with each of the portions of the fractured bone 630, 618 and 632. The bone facing surfaces 924 are anatomic alignment surfaces shaped to match the surface of the reduced fractured bone 610 in a single position and orientation.

During the fracture reduction process, a reduction clamp may be used to hold the reduced portions of bone in place. The guide may include an outward facing surface that is on an opposite side of the body of the guide 900 from the bone facing surfaces 924. The outward facing surface may include a clamp receiving surface that is shaped to receive a portion of a bone reduction clamp.

A doctor may use a bone reduction tool, such as the guide 900, during a fracture repair. For example, after the patient's bone fracture, the doctor may attempt to place the guide 900 in its preoperatively planned installation position and orientation. When placing the guide 900, the doctor attempts to align or engage the patient specific bone facing surfaces 924 with the anatomic structure of the patient and then observe the alignment or misalignment of the patient specific bone facing surfaces 924 with the portions of fractured bone 618, 630, and 632. The alignment or misalignment of the prosthetic alignment surfaces with patient specific bone facing surfaces 924 with the portions of fractured bone 618, 630, and 632 indicates information to the doctor regarding the reduction of the bone fracture. For example, if the patient specific bone facing surfaces 924 aligns with the surface of the portions of fractured bone 618, 630, and 632, then a doctor may know that the bone 601 has been properly reduced, while misaligned alignment of the surfaces may indicate how the position or orientation of one or more of the portions of fractured bone 618, 630, and 632 should be changed to reduce the bone into the final pre-operatively planned reduced position.

The distal ends of the proximal arm 910 and distal arm 920 include respective implant alignment structures 940 for aligning the implant 850 with the bone 610 of the patient in position and orientation determined based on preoperative planning. The implant alignment structures 940 may include one or both of an alignment surface 942 and an engagement structure 944.

The alignment surface 942 is shaped to match the surface of the implant 850. The shape and contours of the implant alignment surface 942 may be determined based upon the bone surface 640 formed from the 3-D modeling images of the patient, a combination of two-dimensional radiographic images of the patient, or a combination of three-dimensional and two-dimensional images of a patient and a final position and orientation of the implant 850.

The engagement structure 944 may be an elongated member or finger that extends into and/or mates with an aperture 852 of the implant. The finger may have a diameter that matches the diameter of the aperture such that the finger engages with the aperture with a running or sliding fit.

In some embodiments, the alignment structure 940, including the engagement structure 944 and alignment surface 942 may form a snap fit with the implant 850 such that when the alignment structure 940 is aligned engaged with the implant 850, the guide 900 is releasably coupled to the implant.

The guide 900, having both an alignment surface that matches the surface of the bone 610 of the patient, e.g., bone facing surfaces 924, and an alignment structure that matches the surface of the implant, e.g., the alignment structure 940, may be used to properly align the implant 850 in a position and orientation that corresponds to a pre-operatively planned position relative to the surface of the bone.

Once the doctor has confirmed that the guide 900 or the implant 850 is properly oriented and located, the doctor can affix the implant 850 to the bone 610 of the patient, for example, by fastening the implant to the bone with screws or other fasteners.

Figure 10:
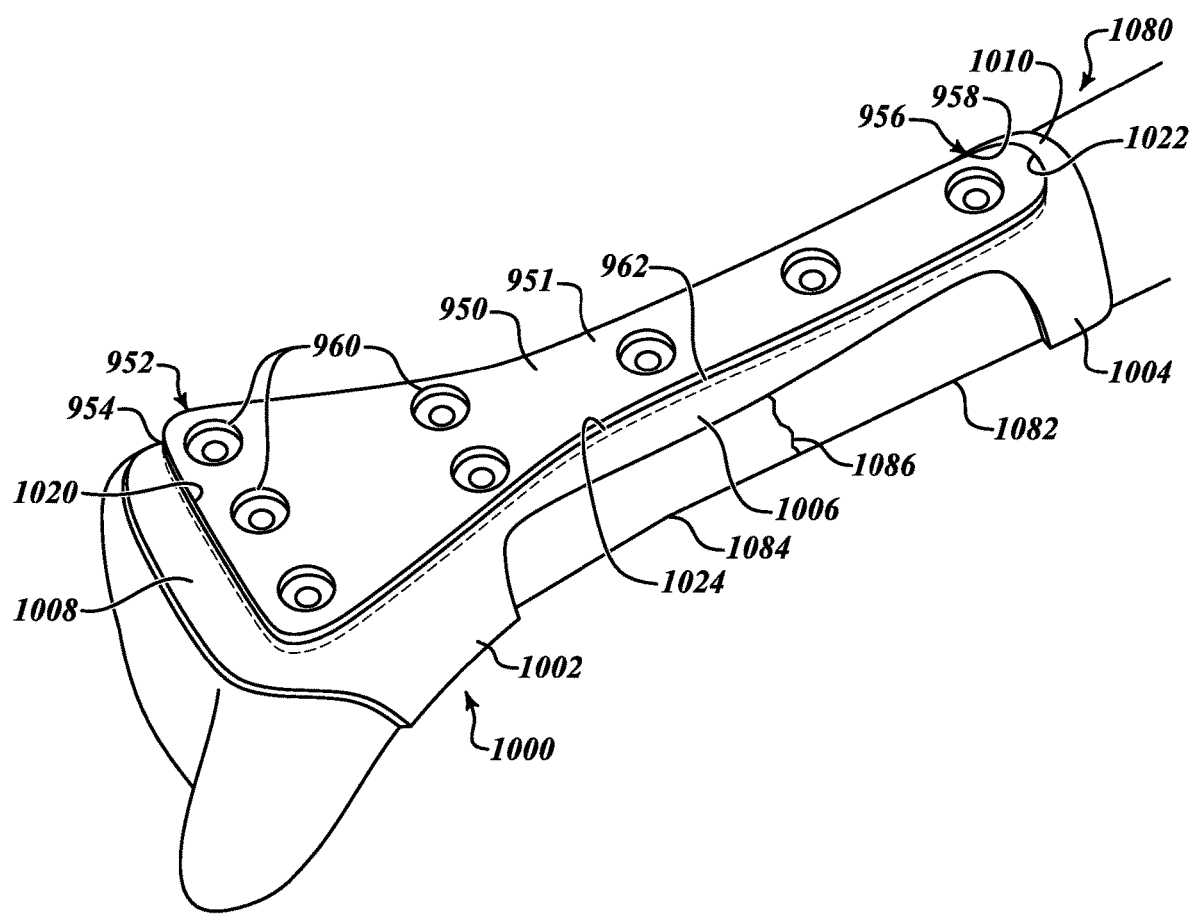
FIG. 10 depicts a view of a tibia with a reduced fracture and an installed patient specific jig and implant according to one or more embodiments disclosed herein.
Figure 11:
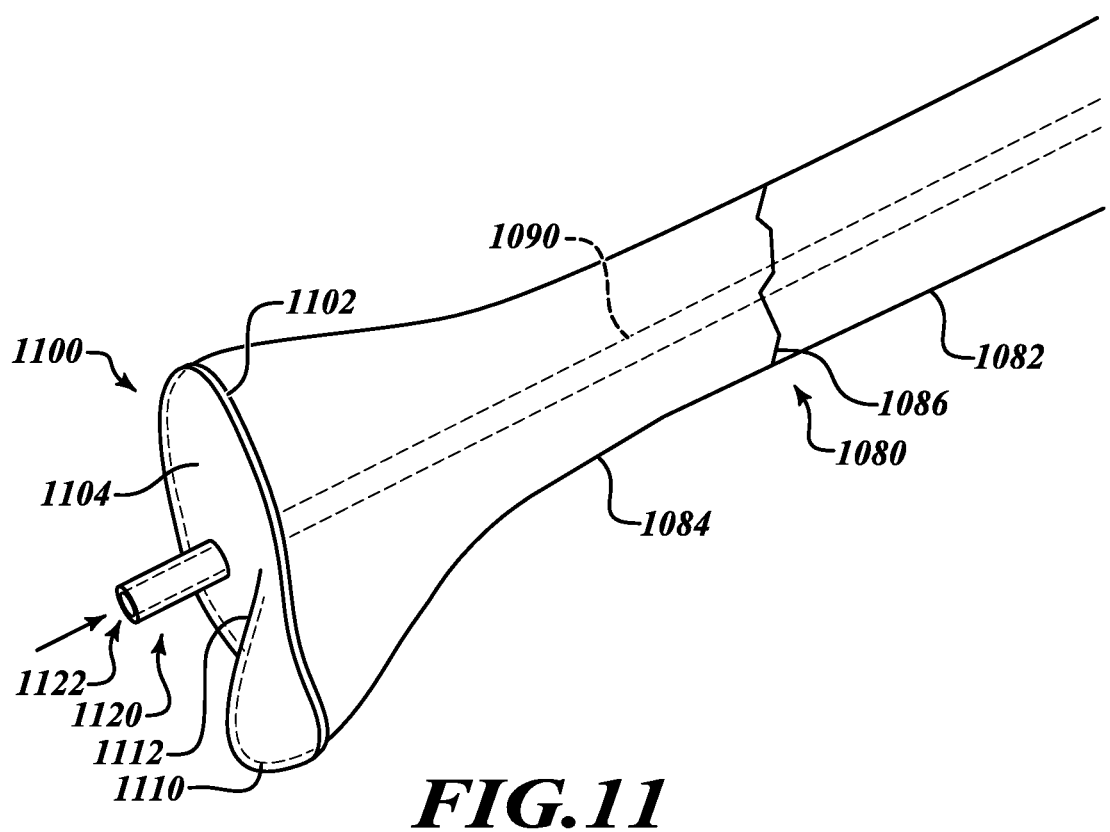
FIG. 11 depicts a view of a tibia with a reduced fracture and an installed patient specific jig and implant according to one or more embodiments disclosed herein.

FIGS. 10 and 11 depict two different patient specific jigs for aligning implants in or on a fractured bone of a patient, in particular a tibia bone. The distal end of the tibia bone 1080 is shown with a reduced fracture 1086 that separates the tibia bone 1080 into two pieces, a distal portion 1084 and a proximal portion 1082. FIG. 10 depicts a patient specific jig 1000 for use in aiding in confirming proper reduction of the bone 1080 and placement of a bone surface mounted implant 950 while FIG. 11 depicts a patient specific jig for use in aiding in the formation of an implant cavity 1090 and in placement of an implant rod, such as an intramedullary rod, into the cavity 1090.

The implant 950 is a surface mounted implant that is coupled or otherwise affixed to the bone of a patient via fasteners inserted though the apertures 960. The implant 950 includes body that extends between a proximal end 956 and a distal end 952 and an outer perimeter 951 or sidewall.

The patient specific jig 1000 includes a main body extending between a distal end 1008 and a proximal end 1010. The patient specific jig 1000 also includes both anatomic and implant alignment structures. For example, the patient specific jig 1000 includes a proximal anatomic alignment structure 1004 and a distal alignment structure 1002.

The anatomic alignment structures 1004, 1002 also includes an alignment surface that conforms or matches the anatomic surface structure of the bone of the patient. For example, one or more alignment structures 1004, 1002 may align or engage with a point or area of bone adjacent the final pre-operative location of the implant 950. The alignment surface may include a surface shape or contours that match the surface shape or contours of the anatomic structure with which the anatomic alignment structures 1004, 1002 aligns.

The shape and contours of the alignment surface may be determined based upon the 3-D modeling images of the patient, a combination of two-dimensional radiographic images of the patient, or a combination of three-dimensional and two-dimensional images of a patient. The shape of the surface is sometimes referred to as a negative of the anatomic structure with which the surface aligns or engages. In some embodiments, the alignment surface aligns or engages with the surface of the bone by nestingly or otherwise mating with the surface of the bone.

The alignment surfaces of respective alignment structures 1004, 1002 may be shaped to match respective portions of the distal and proximal portions of the fractured bone when the fractured bone 1080 is properly reduced. By aligning the alignment surfaces with respective points or areas surrounding the fracture 1086 of the bone, the patient specific jig may confirm proper reduction of the fracture 1086 and aid in placing the implant, as discussed herein.

A patient specific jig may include one or more implant alignment structures. For example, the patient specific jig 1000 includes three implant alignment structures 1020, 1022, 1024. The implant alignment structures 1020, 1022, 1024 may include alignment surfaces that mate with respective portions of the implant 950. For example, the implant alignment structure 1020 may be shaped to match the shape of the outer perimeter 954 of the distal end 952 of the implant 950 while the implant alignment structure 1022 may be shaped to match the shape of the outer perimeter 958 of the proximal end 956 of the implant 950 and the implant alignment structure 1024 may be shaped to match the shape of the outer perimeter 962 of a side of the implant 950 that extends between the distal and proximal ends of the implant. The alignment structures 1020, 1022, 1024 may nestingly or otherwise mate with the corresponding surfaces of the implant.

The shape and contours of the alignment structures 1020, 1022, 1024 may be determined based upon the 3-D modeling images of the patient, a combination of two-dimensional radiographic images of the patient, or a combination of three-dimensional and two-dimensional images of a patient and surface shape of the implant 950. For example, a patient-specific device generator may generate an implant image in its final affixed position and orientation and then generate a patient specific jig corresponding to the final implanted position. In such an embodiment, the anatomic alignment structures 1004, 1002 and their corresponding anatomic alignment surfaces may be generated to align or engage with the anatomic structures of the patient near the implant location on the bone of the patient while the implant alignment structures 1020, 1022, 1024 and their corresponding alignment surfaces may be generated to align with the one or more surfaces of the implant when in the final affixed position. In this way, a doctor may use a physical patient specific jig manufactured according to the final installation position of the implant and the patient's specific anatomic structure.

A doctor may use a patient specific jig, such as the patient specific jig 1000, during a fracture repair operation. For example, after reducing the patient's tibia, the doctor may place the patient specific jig 1000 on the tibia to confirm proper reduction of the fracture. Then the doctor may insert the implant into the patient specific jig and to place the implant in a final affixed position and orientation. After placing the implant, a doctor may align or engage the patient specific jig, such as patient specific jig 1000, with the anatomic structure of the patient and then observe the alignment or misalignment of the alignment structures and implant alignment surfaces with the outer perimeter or other portion of the implant. The alignment or misalignment of the implant alignment surfaces with the outer perimeter or other portion of the prosthetic indicate information to the doctor regarding the position of the implant and the reduction of the fracture. For example, if the anatomic alignment surfaces do not align properly with the corresponding portions of the bone of the patient, then this may indicate to the doctor that further reduction or refinement of the reduction of the fracture should be carried out to properly reduce the bone fracture, according to the preoperative planning.

Once the doctor has confirmed that the patient specific jig 1000 or the implant 950 is properly oriented and located, the doctor can affix the implant 950 to the bone 1080 of the patient, for example, by fastening the implant to the bone with screws or other fasteners.

FIG. 11 shows a patient specific jig for aiding in placing a intramedullary rod into a bone of a patient. The patient specific jig 1100 is formed according to bone surface image from image data from the fractured bone structure of a patient. In FIG. 11, the bone 1080 of the patent has already been reduced and proper reduction confirmed using one or more of the devices described herein for aiding in reducing and confirming proper reduction of a fractured bone. The patient specific jig 1100 aids in fixing the reduced bone and proper alignment of the rod aids in a healthy and strong healing of the bone.

The patient specific jig 1100 may include a main body formed between a bone facing, patient specific surface 1102 and an outward facing surface 1104. The patient specific surface may be formed based on pre-operative imaging and generated surface models of the bone of the patient. For example, the bone facing surface 1102 of the patient specific jig 1100 includes an edge that matches the edge formed between the articular surface and the medial malleolus of the tibia of the patient and a cavity 1110 for receiving the medial malleolus of the tibia of the patient. By aligning the patient specific surface 1102 with the edge formed between the articular surface and the medial malleolus of the tibia of the patient and/or the medial malleolus of the tibia of the patient, the patient specific jig is aligned in a single position and orientation on the bone of the patient.

Once properly aligned, the doctor can use the rod guide 1120 to aid in forming the channel or blind shaft 1090 for receiving the intramedullary rod. The rod guide 1120 extends from the outward facing surface of the patient specific jig 1100 and includes an aperture 1122 that extends from the patient specific surface 1102 to a distal end of the rod guide 1120. The aperture has a central axis that is coaxial with the central axis of the channel 1090, accordingly to the pre-operatively planned installation position of the intramedullary rod.

Figure 12A:
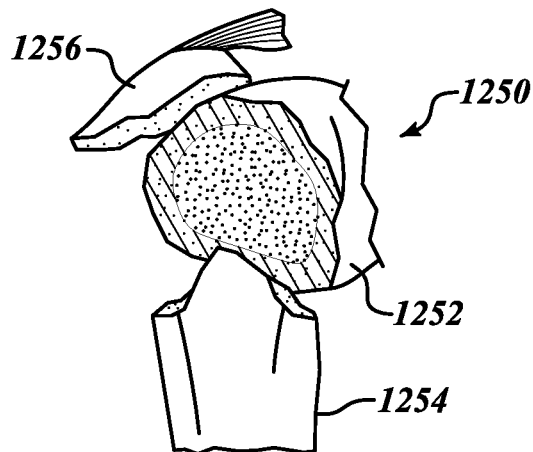
FIG. 12A shows a fractured shoulder according to one or more embodiments disclosed herein.
Figure 12B:
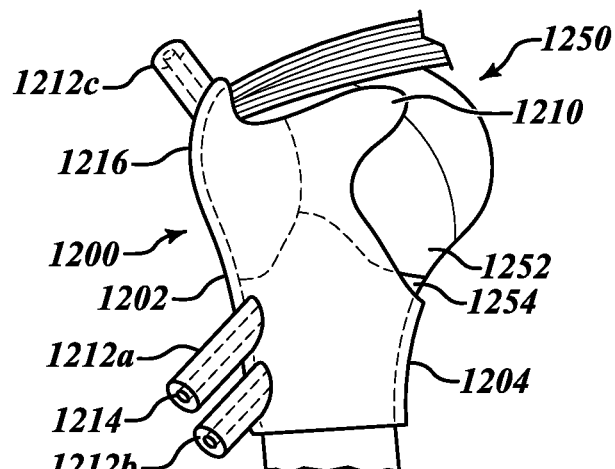
FIG. 12B shows a reduced fractured shoulder with an installed patient specific jig according to one or more embodiments disclosed herein.
Figure 12C:
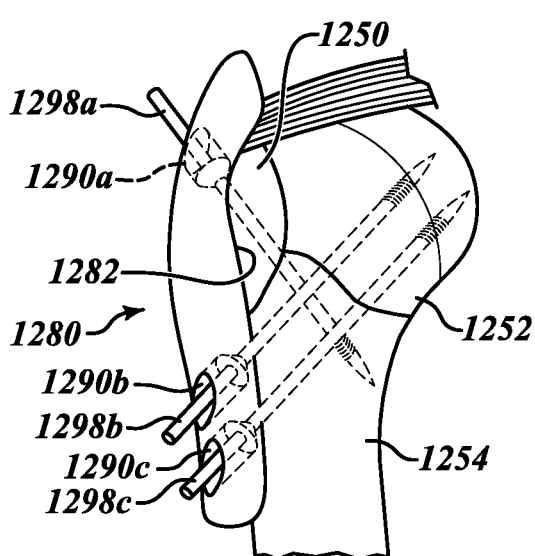
FIG. 12C shows a reduced fractured shoulder with an installed patient specific jig according to one or more embodiments disclosed herein.

FIGS. 12A, 12B, 12C show the reduction of a fractured humerus 1250. As shown in FIG. 12A the humerus 1250 is fractured into three pieces, the head 1252, the shaft 1254, and the greater tuberosity 1256 with fractures separating the greater tuberosity 1256 from the head 1252 and the shaft 1254 and a fracture though the anatomical neck.

FIG. 12B shows the fractured humerus 1250 after reduction with a patient specific jig 1200 placed on the humerus 1250. The patient specific jig 1200 is one or both of a bone reduction tool or implant alignment guide. As a bone reduction tool, the patient specific jig includes one or more anatomic alignment members 1204, 1210, 1216 that are shaped to match the shape of respective portion of the humerus 1250 after proper reduction of the fracture.

The anatomic alignment structures 1204, 1210, 1216 include an alignment surface that conforms or matches the anatomic surface structure of the bone of the patient. For example, one or more alignment structures 1204, 1210, 1216 may align or engage with a respective point or area of bone according to a pre-operatively planned reduction of the fracture. For example, alignment structure 1204 includes a bone facing, patient specific alignment surface that corresponds to the shape of a portion of the shaft 1254 of the humerus, the alignment structure 1210 includes a bone facing, patient specific alignment surface that corresponds to the shape of a portion of the head 1252 of the humerus, and the alignment structure 1216 includes a bone facing, patient specific alignment surface that corresponds to the shape of a portion of the greater tuberosity 1256 of the humerus. The alignment surfaces may include a surface shape or contours that match the surface shape or contours of the anatomic structure with which the anatomic alignment structures 1204, 1210, 1216 aligns. By aligning the alignment surfaces with respective points or areas surrounding the fractures of the humerus, the patient specific jig may confirm proper reduction of the fracture and aid in placing the implants, as discussed herein.

The shape and contours of the alignment surface may be determined based upon the 3-D modeling images of the patient, a combination of two-dimensional radiographic images of the patient, or a combination of three-dimensional and two-dimensional images of a patient. The shape of the surface is sometimes referred to as a negative of the anatomic structure with which the surface aligns or engages. In some embodiments, the alignment surface aligns or engages with the surface of the bone by nestingly or otherwise mating with the surface of the bone.

A patient specific jig may include one or more implant alignment structures. For example, the patient specific jig 1000 includes three implant alignment structures 1212*a*, 1212*b*, 1212*c*. The implant alignment structures 1212*a*, 1212*b*, 1212*c* are rod guides that extend from the outward facing surface of the patient specific jig 1200 and each rod guide includes an aperture 1214 that extends from the bone facing surface 1102 to a distal end of the rod guide 1120. The aperture has a central axis that is coaxial with the installation axis of implant pins used to fix the reduced fractured bone. The installation axis is determined accordingly to the pre-operatively planned installation position of the implant pins.

The shape and contours of the alignment structures 1204, 1210, 1216 may be determined based upon the 3-D modeling images of the patient, a combination of two-dimensional radiographic images of the patient, or a combination of three-dimensional and two-dimensional images of a patient and surface shape, position, and orientation of the implant pins. For example, a patient-specific device generator may generate an implant image in its final installed position and orientation and then generate a patient specific jig corresponding to the final implanted position. In such an embodiment, the anatomic alignment structures 1204, 1210, 1216 and their corresponding anatomic alignment surfaces may be generated to align or engage with the anatomic structures of the patient near the implant location on the bone of the patient while the implant alignment structures 1212*a*, 1212*b*, 1212*c* may be generated to align with the one or more surfaces or installation axis of the implant when in the final affixed position. In this way, a doctor may use a physical patient specific jig manufactured according to the final installation position of the implant and the patient's specific anatomic structure.

Once the doctor has confirmed that the patient specific jig 1200 is properly oriented and located, the doctor can form the holes for the implant rods.

As shown in FIG. 12C, a generic or patient specific implant 1280 may be affixed to the humerus of the patient. The implant may include a patient facing surface 1282 that may mate with the surface of the patient's humerus in a single position and orientation. The implant 1280 also includes apertures 1290*a*, 1290*c*, 1290*c* that are positioned and have an axis orientated according to the preoperatively planned position and orientation of the implant pins 1298*a*, 1298*b*, 1298*c*.

The various embodiments described above can be combined to provide further embodiments. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A device for reducing a fractured bone, the device comprising:
    an implant comprising an outer perimeter having a first portion and a plurality of apertures through the implant shaped to receive fasteners for fixing the implant to the bone;
    a body, separate from the implant, having a bone facing surface shaped to match a shape of a surface of a reduced fractured bone at a location proximate an installation position of the implant; and
    an implant alignment member extending from the body and having a surface shaped to receive the implant in a predetermined orientation and comprising an outer perimeter having a concavity formed therein, the outer perimeter being shaped to match and receive therein a first portion of the outer perimeter of the implant.

2. The device of claim 1, wherein:
    the body comprises an implant coupling shaped to releasably couple the body to the implant.

3. A device for fixing a fractured bone, the device comprising:
    an implant comprising an outer perimeter having a first portion and a plurality of apertures through the implant shaped to receive fasteners for fixing the implant to the bone;
    a body, separate from the implant, extending between a proximal end and a distal end, the body having a patient specific surface shaped to match a surface of a reduced fractured bone of a patient according to three-dimensional surface image data of the bone;
    a proximal arm extending from the proximal end of the body and including an outer perimeter having a first implant alignment structure at a distal end of the arm, the outer perimeter shaped to receive the outer perimeter of the implant therein, the first implant alignment structure also being shaped to correspond to a shape of an outer perimeter of the implant in a final position and orientation according to a pre-operatively planned position; and
    a distal arm extending from the distal end of the body and including a second implant alignment structure at a distal end of the arm, the second implant alignment structure having a surface shaped to correspond to a shape of a second portion of an implant in a final position and orientation according to a pre-operatively planned position.

4. The device of claim 3, wherein:
the first implant alignment structure is an open alignment structure and the outer perimeter is shaped to correspond with a shape of an outer sidewall of the first portion of the implant.

5. The device of claim 4, wherein:
the second implant alignment structure is a closed alignment structure having an alignment surface shaped to correspond with a shape of a sidewall and outward facing surface of the second portion of the implant.

* * * * *